United States Patent [19]

Weed et al.

[11] 4,317,078
[45] Feb. 23, 1982

[54] REMOTE POSITION AND ORIENTATION DETECTION EMPLOYING MAGNETIC FLUX LINKAGE

[75] Inventors: Herman R. Weed, Columbus, Ohio; Ram M. Engira, Ludhiana, India

[73] Assignee: Ohio State University Research Foundation, Columbus, Ohio

[21] Appl. No.: 84,869

[22] Filed: Oct. 15, 1979

[51] Int. Cl.³ .............................................. G01B 7/14
[52] U.S. Cl. ..................................... 324/208; 128/653
[58] Field of Search ............... 324/207, 208, 228, 239, 324/243, 244, 246; 340/686; 128/639–644, 653, 654

[56] References Cited

U.S. PATENT DOCUMENTS

| | | | |
|---|---|---|---|
| 3,526,886 | 9/1970 | Lubich | 324/207 |
| 3,868,565 | 2/1975 | Kuipers | 324/207 |
| 4,054,881 | 10/1977 | Raab | 324/244 |

Primary Examiner—Gerard R. Strecker
Assistant Examiner—Walter E. Snow
Attorney, Agent, or Firm—Millard & Cox

[57] ABSTRACT

The process and system for locating the position and orientation of an implement in space wherein a varying magnetic field responsive component (14) such as a coil is positioned upon the implement. A magnetic field source (12) excitable from an a.c. source derives alternating flux fields which are moved along or parallel to coordinate axes established at a reference plane. The coordinate position of the sensor is derived by determining the positions of minima and maxima flux linkage during magnetic field source movement.

32 Claims, 26 Drawing Figures

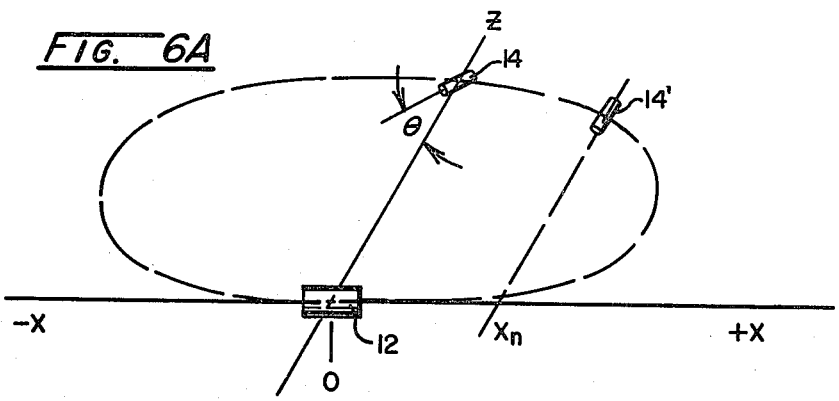
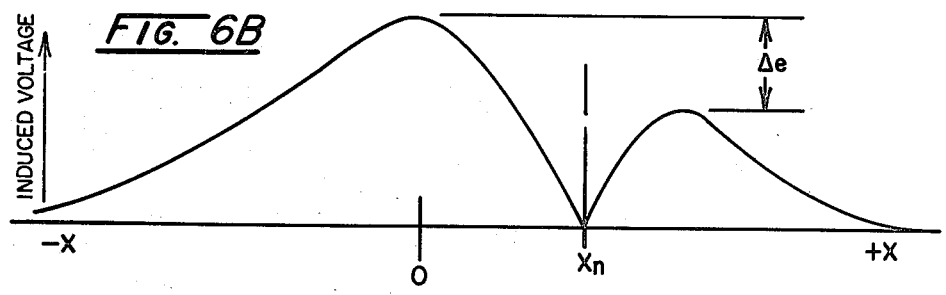
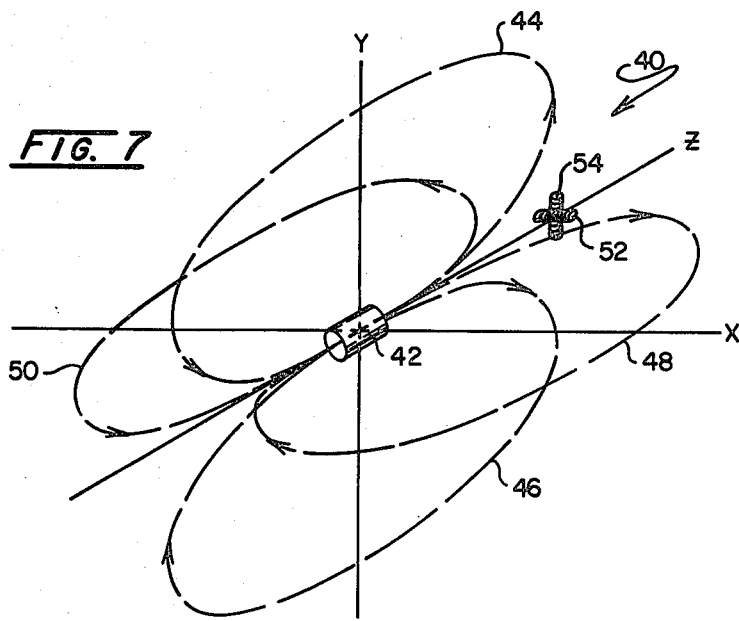

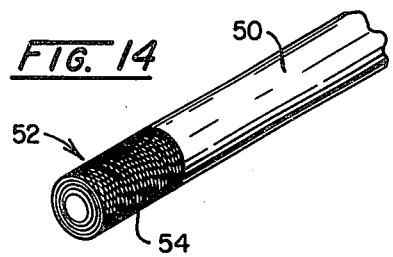
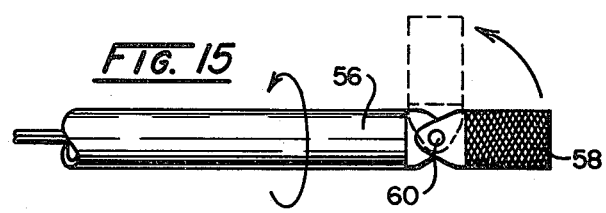
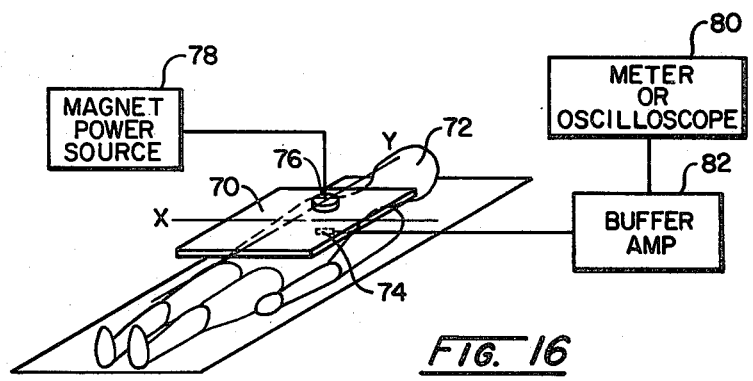
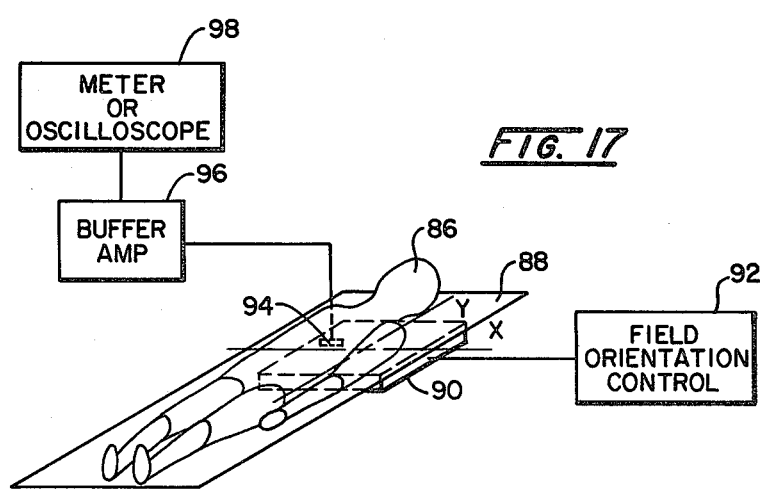

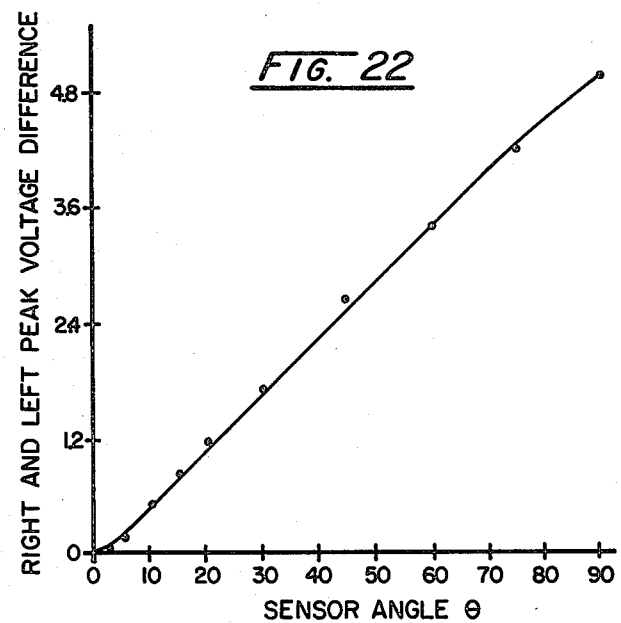
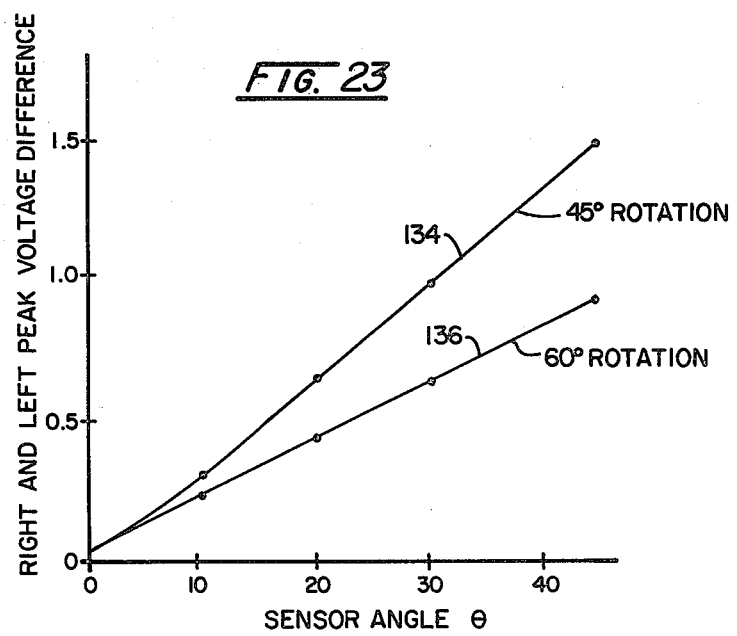

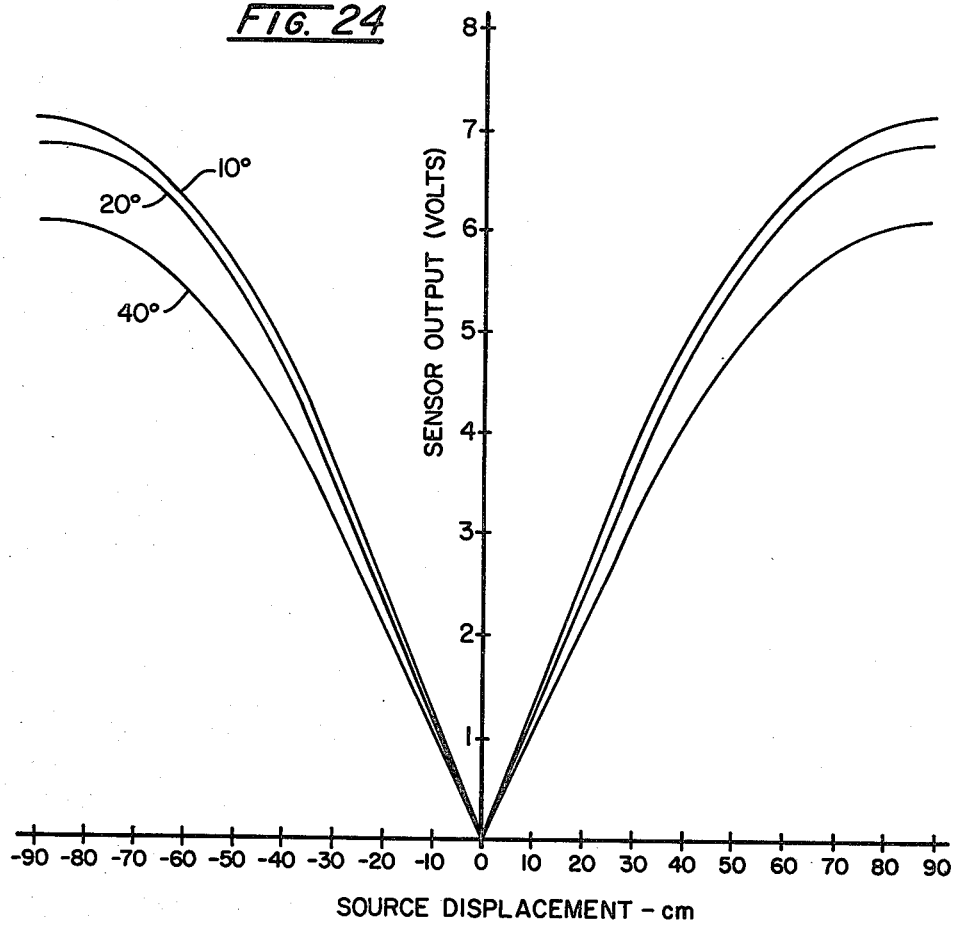

REMOTE POSITION AND ORIENTATION DETECTION EMPLOYING MAGNETIC FLUX LINKAGE

The government has rights in this invention pursuant to Grant Number DAR-77-11665 awarded by the National Science Foundation.

BACKGROUND OF THE INVENTION

Techniques by which objects are located in three dimensional space span a broad range of scientific disciplines, the most typical involving optical or wave energy triangulation procedures and the like. The nature of the three dimensional space involved generally is primarily determinative of the approach taken by investigators in developing a mapping technique. Thus, visual access to the space, the conductive or magnetic character thereof and other aspects have a bearing upon the technical approaches taken.

Technologic developments in the field of medicine have involved the manipulation, in vivo or in vitro, of a wide variety of diagnostic and therapeutic probes and/or components through body tissues and cavities. This manipulation often requires an accurate monitoring of the location of such devices without incurring concomitant adverse influence upon the body tissue itself. In the latter regard, an avoidance of potentially damaging radiation interaction with the tissue may be important.

Medical procedures requiring a close, in vivo, monitoring of probe or component locations are those for example involving the use of heart catheters, coronary artery catheters or other internal body sensors. To avoid resort to open-heart surgery, a "pacemaker" type stimulator may be moved by catheters along a vena cava to the heart whereupon implantation is carried out by screw-attachment to muscle tissue. Power supply for the thus implanted stimulator then is more conveniently itself implanted for accessibility remote from the heart within the upper chest cavity. To the present, fluoroscopy, involving relatively higher levels of radiation is used to carry out probe position monitoring. Therapy involving the in vivo positioning of radioactive sources also requires precise position monitoring procedures to assure appropriate interaction of tissue being treated with emanating radiation. Where such implantation or probe positioning procedures are carried out, it is desirable that a precise monitoring of probe location be provided using a technique wherein accuracy is achieved without use of potentially harmful imaging or mapping systems.

SUMMARY OF THE INVENTION

The present invention is addressed to a process and a system for locating the position in space of an object without use of radiation or ultrasound energy. This process associates alternating magnetic flux fields of predetermined shape with the output signals of a varying magnetic field responsive sensor in a manner wherein, upon carrying out effective relative movement between these two components, the location in three-dimensional space of one or the other readily is determined. Inasmuch as low level magnetic fields are utilized, the location of objects such as catheters and the like within animals or humans may be accurately monitored without ionization or ultrasonic damage to tissue.

In a preferred embodiment, the process provides a sensor present as a varying magnetic field responsive component or winding which is configured for deriving an output signal in the presence of a magnetic flux linkage and in correspondence with the status of an orientation axis thereof. Where present as a winding, the coils thereof preferably are substantially symmetrically disposed about this orientation axis. A magnetic field source is provided which is excitable from an alternating current source to derive alternating magnetic flux fields and this source is prositioned at or with respect to a reference plane within which are established first and second intersecting axes for identifying the position of the sensor. The plane is located adjacent the space within which the sensor is disposed. With the procedure, the magnetic field source is effectively moved with respect to a first axis at the plane in a manner wherein the field is substantially symmetrically disposed about the axis and the operator determines, from the output signals of the sensor, locations along the first axis representing a first null point of substantially no flux linkage and those first and second locations on each side of the first null point representing maximum flux linkages. Upon determining these data, the magnetic field source is effectively moved with respect to the second axis and the reference plane in a manner wherein the magnetic field is substantially symmetrically disposed about its locus of travel and the sensor output signals are monitored to determine locations with respect to the second axis representing the second null point of substantially no flux linkage and those third and fourth locations on each side of the second null point representing maximum flux linkage.

With only two such scans or manipulations of the magnetic field source, the sensor position and orientation may be determined. For instance, the sensor position geometrically most proximate the first axis is determined in correspondence with the first null point location and the magnitude of the difference between the sensor output values for the first and second locations representing maximum flux linkage. Additionally, those sensor positions geometrically most proximate the second axis are determined in correspondence with the second null point location and the magnitude of the difference between the sensor output values for the third and fourth locations representing maximum flux linkage. Finally, the distance of the sensor from the reference plane is determined in correspondence with the location of a null point, an adjacent location of maximum flux linkage and a corresponding difference between the magnitude of the maximum sensor output values associated with a given one of the first or second axes. The functional roles of the magnetic source and the sensor component may be reversed.

As another feature and object of the invention, the above process is carried out in a manner utilizing a sensor, the orientation axis of which may be adjusted by the operator so as to provide a predetermined geometry of the component with respect to the established reference plane. With this procedure, adjustment is made to the sensor in each of two orthogonal orientations to provide equal values of maximum flux linkage as are associated upon opposite sides of a given null point. Where catheters are utilized in conjunction with this process, the catheters may be rotated to provide one angular orientation of the sensor and the sensor may be pivotally moved upon the catheter to provide the next orientation thereof with respect to the reference plane.

As another feature and object of the invention, the above process is carried out wherein the magnetic field source is provided as a solenoid having an axis of field orientation about which the alternating magnetic flux fields are symmetrically disposed. This field orientation axis is arranged so as to be substantially perpendicular to the reference plane. For this orientation, the sensor component, when configured as a winding substantially symmetrically disposed about an orientation axis, is disposed such that the orientation axis is in parallel relationship with the reference plane. The sensor component axis of orientation is arranged generally in parallel with the first axis when the magnetic field source is moved therealong and is oriented generally in parallel with the second axis when the magnetic field source is effectively moved in parallel with that second axis. Alternately, two sensor cells having transversely oriented axes may be utilized for this approach. Due to enhanced magnetic field gradients, this approach also provides a higher sensitivity in deriving sensor output signals.

Other objects of the invention will, in part, be obvious and will, in part, appear hereinafter.

The invention, accordingly, comprises the method and system posessing the construciton, combination of elements and steps which are exemplified in the following detailed disclosure. For a fuller understanding of the nature and objects of the invention, reference should be had to the following detailed description taken in connection with the accompanying drawings.

BRIEF DESCRIPTION OF THE DRAWINGS

FIG. 6A is an idealized diagrammatic representation utilized in describing the effects of angular variations in the axis of symmetry of a sensor;

FIG. 6B is a representation induced voltage output characteristic curve for the sensor described in conjunction with FIG. 6A;

FIG. 7 is an idealized diagrammatic representation of a source coil and sensor arrangement representing another embodiment of the invention;

FIG. 14 is a pictorial representation of a catheter incorporating a sensor according to the invention;

FIG. 15 is a pictorial partial view of a catheter including a sensor and fabricated in accordance with the teachings of the invention;

FIG. 16 is a schematic representation of one implementation of the teachings of the invention;

FIG. 17 is a schematic representation of another, semi-automatic implementation of the system and method of the invention;

FIG. 22 shows a curve correlating variations in sensor angle with right and left maxima voltage differences as developed by a sensor according to the invention;

FIG. 23 shows data as compiled in connection with FIG. 22 but for different degrees of rotation of the source coil; and FIG. 24 shows a family of curves depicting induced sensor output voltage as related to source displacement for variations in the angle of the source coil axis of symmetry with respect to the reference plane.

DETAILED DESCRIPTION OF THE INVENTION

The present invention involves a technique wherein a created magnetic field is utilized to accurately determine the position and orientation of an object in three-dimensional space. Location of the object is carried out utilizing a sensor which may be present as a symmetrical winding. This winding may be so small as to be carried upon a catheter or similar probe as is conventionally utilized in the biomedical field. The 3-dimensional space within which the sensor may be located should be "non-magnetic" at least in the sense that the created magnetic field remains predictable. Thus, the location finding arrangement of the invention may be utilized in air, water, ceramics, plastics, wood and the like as well as in conjunction with animal tissue or flesh. In the latter regard, a magnetic field strength may be employed which is lower than that of earth's magnetic field by several orders of magnitude and, thus, the method and system is ideally harmless to that tissue.

Figure 1:
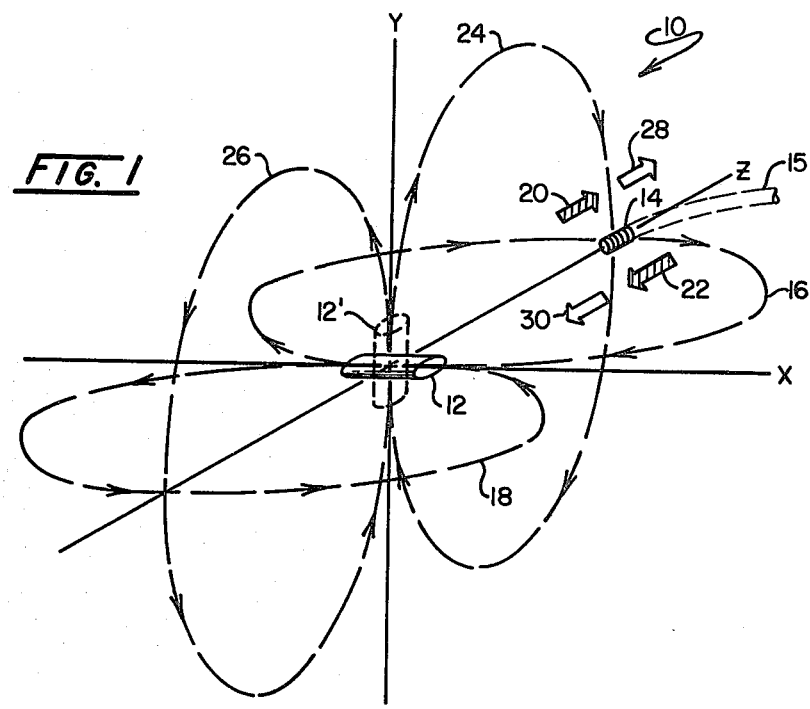
FIG. 1 is a diagrammatic representation of a source coil and sensor as utilized in conjunction with the invention, additionally showing idealized magnetic flux paths for two source coil orientations.

Looking to FIG. 1, an initial aspect of the invention may be described in connection with a schematic representation of x, y and z axes which are mutually orthogonally disposed and establish coordinates in space generally designated at 10. Disposed within that space are a symmetrically wound solenoid winding 12 and a sensor coil 14, the windings of each of which are symmetrically wound about a longitudinal or orientation axis extending therethrough. Sensor coil 14 is shown attached to the probe 15 such as a catheter and is disposed having its longitudinal or orientation axis coincident with the z axis, while solenoid winding 12 is disposed such that its longitudinal or orientation axis about which the windings thereof are symmetrically provided is coincident with the x axis. When the winding of solenoid 12 is excited with an alternating electrical source of voltage or current, a magnetic field having lines of flux, for example as represented by dashed lines 16 and 18, is generated. The characteristics of magnetic fields thus generated are described in detail in the literature, reference being made to the text: "Elecromagnetics" by J. D. Kraus, McGraw-Hill Book Company, Inc. (1953). The basic relationship for that magnetic flux density which would occur at a given point, for example along flux line 16 or 18 as produced by a current carrying elemental portion of a winding of length, dl, is given as follows:

$$dB = k\, I\, dl\, \sin \theta / r^2$$

where:
dB = infinitesimal flux density at the point in question,
I = current in the element,
$\theta$ = the angle between the current direction and the radius vector from the elemental component to the point considered, and
r = the distance from that elemental component to the position desired.

The quantity, k, is a constant of proportionality given by the relationship:

$$k = \mu / 4\pi$$

where $\mu$ is the permeability of the medium.

Assuming that the medium 10 has a uniform permeability and substituting the above value for k, the following expression is obtained:

$$dB = \mu I\, dl\, \sin \theta / 4\pi r^2$$

The above expression is often referred to as the Biot-Savart law. The direction of dB is everywhere normal to the lengthwise extent of the element of length dl and dB is thus a vector.

The symmetry of the windings of solenoid 12, for example about the x axis, achieves a field which is predictable and which reverses upon the half-cycle of alternating current excitation thereof. Looking now to sensor coil 14, Faraday's law provides that an emf is induced within the closed circuit represented by the winding due to a change of any magnetic flux which links it. Thus, the sensor 14 will be linked by magnetic flux, however, such linkage will be only by those components of that magnetic flux which are in parallel with the z axis for the orientation shown. Conversely, those components of flux which are perpendicular to the z axis will not link the turns of sensor coil 14, i.e. the coil winding is decoupled with respect to that component in view of the quadrature relationship between the orientation of the sensor windings with respect to their central or longitudinal axis and the orientation of the flux lines. In effect, for the illustration shown, the magnetic field may be considered as made up of two vectors one parallel to the x axis and one parallel to the z axis. The former represents the "longitudinal component" and the latter, the "radial component". For the orientation shown for sensor 14 in FIG. 1, the field passes through a zero slope or line of constant potential as it crosses the central axis of coil 14. Thus, the *radial component* of flux on one side of sensor 14 as represented by arrow 20 is in one direction, while that on the opposite side thereof as represented by arrow 22 is in an opposite direction. While both such components will induce a voltage, the voltages will be of equal magnitude and of opposite sense to provide an effective zero output of induced voltage at winding 14 at the position shown. Note, that the radial component 20 is positioned at one side of the y-z plane, while the radial component 22 is positioned on the opposite side thereof.

Figure 2:
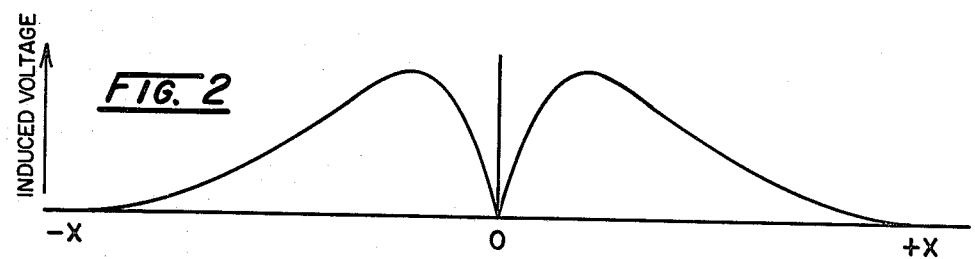
FIG. 2 is an idealized sensor output characteristic curve describing the operation of the representation of FIG. 1 with a winding 12 orientation.

From the foregoing, it will be apparent that the slightest movement either of solenoid 12 on the x-y plane along the x axis or the sensor 14 will result in a net flux change and thus a net voltage. Therefore, movement of solenoid source coil 12 along the x axis will cause sensor 14 to exhibit an induced voltage which is zero (null point) at the position shown wherein sensor 14 and solenoid 12 are aligned along the z axis, i.e. a position wherein the solenoid 12 is geometrically most proximate sensor 14, and which will pass through maximum levels of flux density linkage upon movement in either direction from such null point. The induced voltage will progressively diminish with flux density diminution as the solenoid 12 moves further away from sensor coil 14. A representative plot of such induced voltage with respect to position along the x axis either in a ± direction is revealed in FIG. 2, it being understood, of course, that the plus or minus values will be inverted for each half-cycle of excitation of solenoid 12.

Figure 4:
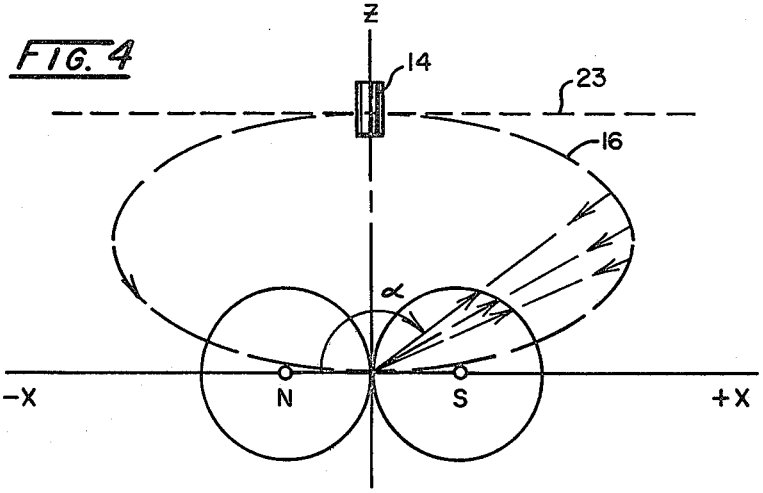
FIG. 4 is a chart showing variations in radial field components for a given source coil.

Looking additionally to FIG. 4, another schematic representation of the abrupt reversal of the radial component of the magnetic field with respect to the z, or "transverse" axis, is depicted in conjunction with the well defined distribution of magnetic field in space surrounding a dipole. Considering sensor 14 to move along locus 23, the figure shows the variation of the magnitude of the radical component with angular variation, $\alpha$, which may be observed to permit the difference detection scheme utilized, inter alia, by the technique of the invention.

Figure 3:
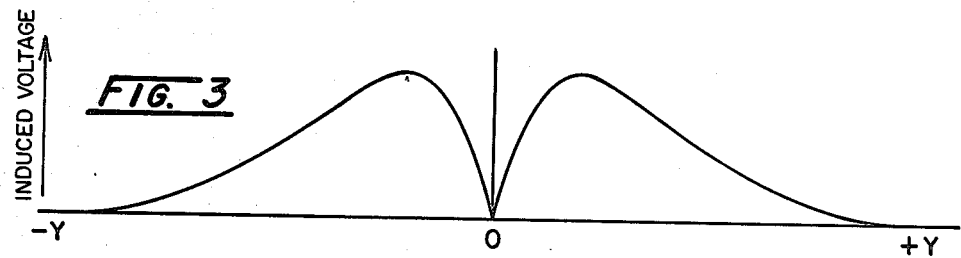
FIG. 3 is another idealized sensor output characteristic curve describing the operation of the representation of FIG. 1 with a winding 12' orientation.

Returning to FIGS. 1 and 2, a first aspect of the location detection arrangement of the invention then is provided with the movement of the solenoid winding 12 along the x axis to determine the location of a null point in induced voltage. By physically reorienting the axis of symmetry of solenoid 12 to parallel relation with the y axis, as represented at 12' in FIG. 1, a magnetic field as represented by flux paths 24 and 26 is derived which will develop representative radial flux components as typified, for example, by arrows 28 and 30. Movement of the solenoid on the x-y plane in its orientation 12' along or in parallel with the y axis will develop induced voltages as represented at FIG. 3 having a zero value at a null point wherein the solenoid 12' is geometrically most proximate to sensor 14 and passing through maxima in similar fashion as the corresponding movement along the x axis represented in FIG. 2. Thus, another parameter for location detection is achieved, and a third or depth parameter as measured parallel with the z axis is next required. In the latter regard, it has been determined that the positions of the above-noted maxima bear direct relationship with the depth value, d, as measured from the x-y plane to the position of sensor 14.

Figure 5A:
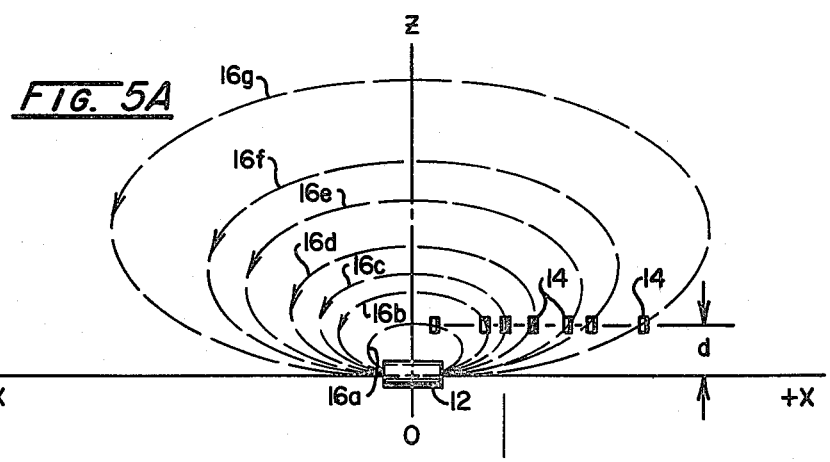
FIG. 5A is an idealized diagrammatic representation utilized in the description of the procedure for developing depth data in accordance with the teachings of the invention.
Figure 5B:
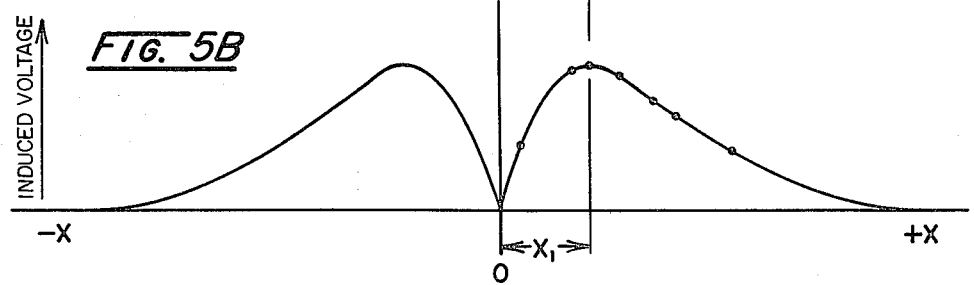
FIG. 5B is an idealized sensor output characteristic curve associated in alignment with the diagrammatic representation of FIG. 5A.
Figure 8:
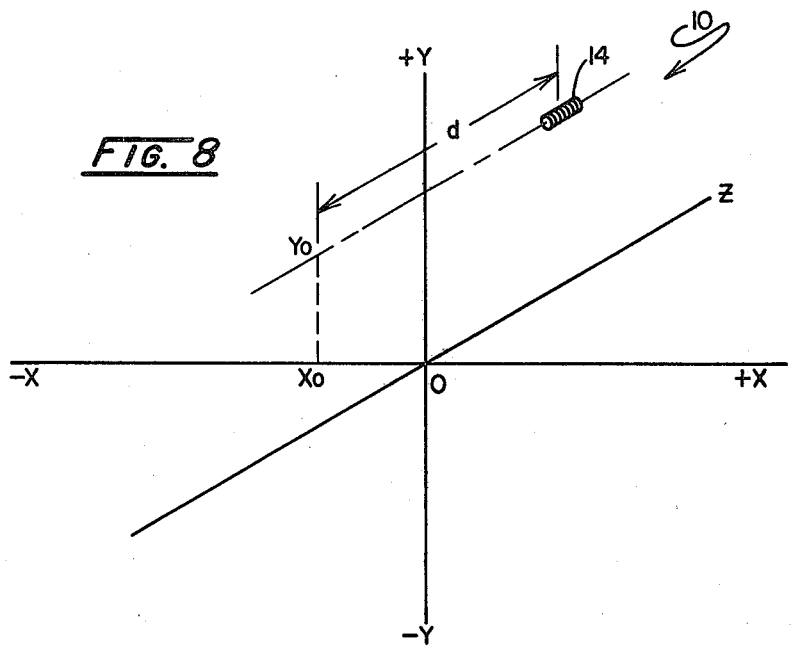
FIG. 8 is a diagrammatic representation of a source coil positioned at an arbitrary coordinatized location within three-dimensional space.

Looking additionally to FIG. 5A, a schematic representation of the x axis, solenoid winding 12 and a variety of positions for sensor coil 14 are revealed. The figure also incorporates a series of representative flux paths 16a–16g. To facilitate an understanding of the depth detection technique at hand, sensor 14 is assumed to be moved while solenoid 12 is retained in the orientation shown in FIG. 1. (hereinafter referred to as the "inverted T" orientation). This assumed movement is from the positions adjacent the z axis outwardly in parallel with the positive portion of the x axis. Note, that as the sensor would be moved in the latter direction, as it reaches a flux linking position with respect to flux path 16c, the *radial component* of that path is in parallel with the longitudinal axis of symmetry of the sensor 14 winding. At this point, a maximum linkage is achieved. Note, that the movement of sensor 14 is along a locus parallel with the x axis at the desired depth value, d. Looking additionally to FIG. 5B, it may be observed that the induced voltage maximum value will be observed to correspond with the position of maximum flux linkage represented at path 16c. It has been found that the distance, $x_1$ from the triaxis ordinate to this position is directly related to depth, d, as calibrated by a constant. Thus, the principal three parameters deriving the three-dimensional location of sensor 14 with respect to the x-y plane is achieved. Of course, for the technique as thus described, the axis of symmetry of sensor coil 14 is aligned with the z axis of the coordinate system.

In many applications of the invention, the orientation of sensor winding 14 with respect to the orientation of the plane upon which solenoid winding 12 is effectively manipulated will not be known. Thus, it becomes necessary to evolve a technique wherein the orientation of sensor 14 can be both determined and accommodated for in developing the appropriate coordinates identifying its position.

Turning to FIG. 6A, solenoid 12 again is shown having its axis of symmetry or longitudinal axis aligned with the x axis and sensor coil 14 is shown having an orientation falling within the x-z plane but oriented such that its axis of orientation or symmetry resides at an angle θ with respect to the z axis. Assuming that solenoid 12 has been moved such that the relative position (minimum output position) of sensor 14 within the thus generated magnetic field now falls at position 14', a null point will be achieved in the same manner as described in connection with FIGS. 1 and 2, but that null point will be located at position $x_n$ which is displaced from the origin of the x, y, z reference axes. The field generated by solenoid 12 will no longer be symmetrical about that null point, $x_n$, inasmuch as it is displaced from the origin. For the pitch orientation shown, sensor 14' no longer being in the center of the magnetic field, will link to define a maximum induced voltage with flux paths of lower flux density. The induced voltage maxima generated from the movement of sensor 12 along the x axis are no longer equal in magnitude. Referring additionally to FIG. 6B, it may be observed that the null point for the induced voltage readout of sensor 14 for the present condition is displaced from the ordinate, 0, to position $x_n$ and that the maxima exhibit a difference in magnitude, $\Delta_e$. This difference in magnitude, $\Delta_e$, is directly related to the angle θ. As is apparent, by reorienting solenoid winding 12 to move along (i.e. with respect to) the y axis in a manner earlier described a corresponding angle of sensor 14 with respect to that axis may be determined.

Referring to FIG. 7, a schematic depiction of an alternate technique for sensor location is provided. In the figure, a medium is generally represented at 40 within which are defined x, y and z axes, the x-y axes falling within a reference plane. A solenoid 42 having its winding symmetrically disposed about its longitudinal or orientation axis is positioned at the ordinate of the three axes. In this embodiment, however, the axis of symmetry of solenoid 42 is aligned with the z axis such that representative magnetic flux paths in the y-z plane are shown at 44 and 46, while lines of flux generated within the x-z plane are shown at 48 and 50. For this embodiment, the sensor is represented as two symmetrical winding coils 52 and 54, the symmetrical axes of which are oriented perpendicularly to the z axis and parallel to the x-y plane. The term "inverted T" orientation was utilized above to categorize the orientations or geometry of sensor 14 with respect to solenoid 12 shown in FIG. 1. Conversely, the corresponding geometry of the embodiment of FIG. 7 is referred to as a "T" orientation. Recall, that in the embodiment of FIG. 1, the symmetrical axis of the sensor coil is perpendicular to the x-y plane. Note, that sensor coils 52 and 54, for the null position shown, are not within the somewhat "rounded" portion of the magnetic field as in the case of the embodiment of FIG. 1. Now, the reversal of the radial flux about the longitudinal axes or axis of orientation of the sensor winding is utilized to generate location signals. With the arrangement shown, a slight movement of solenoid 42 or sensor coil 52 parallel to the x axis will quickly develop an induced voltage within coil 52, for example, under the influence of field path 48 and out of the influence of path 50. Movement of sensor coil 54 along the y axis, or conversely, movement of solenoid 42 along the axis similarly will bring it under the influence either of paths at 44 or 46 and a greater sensitivity of the system shown to movement of the solenoid or sensor has been observed. However, either an alternation of the orientation of the sensor coil to the positions shown at 52 or 54 is required or the use of a dual coil arrangement as illustrated with appropriate swithing is required. On the other hand, the magnetic field supported by solenoid 42 is appropriately oriented for detection and location of the sensor. As is apparent, the same interrelationships in determining depth and coordinate positioning hold for the embodiment of FIG. 7 as for the embodiment of FIG. 1. The enhanced sensitivity of the alternate arrangement, however, is apparently due to the steeper gradient of the radial portion of the magnetic field utilized.

Figure 9:
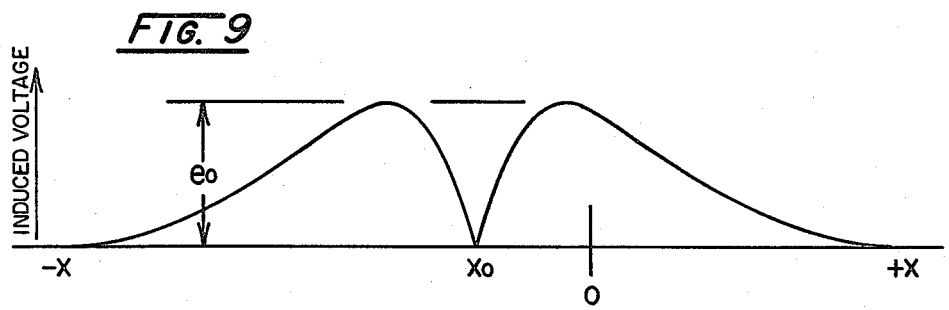
FIG. 9 is an idealized output characteristic curve for the sensor of FIG. 8 (motion along the x axis)

The methods for locating the position of sensor coil 14 may be summarized in conjunction with FIGS. 8–13. Looking to FIG. 8, a first condition is portrayed wherein sensor 14 is shown having its orientation defining axis parallel with a z axis ("inverted T" orientation) extending from the common intersection of x and y axes, the latter axes being formed within a plane which is utilized for reference purposes and upon which a solenoid may be maneuvered either physically or electrically i.e. "effectively". Note, that sensor 14 is positioned a depth, d, behind the x-y reference plane and is at a position $x_0$, $y_0$ with respect to the corresponding established axes at the reference plane. By moving the solenoid (not shown), effectively and properly oriented along the x axis within the reference plane, an induced voltage pattern as represented at FIG. 9 will be evolved. Because of the perpendicular position of the orientation defining axis of sensor 14, the induced voltage maxima $e_O$ are equal and a null point will be achieved as the solenoid effectively is positioned at position $x_0$. Thus, the $x_0$ position of sensor 14 is located.

Figure 10:
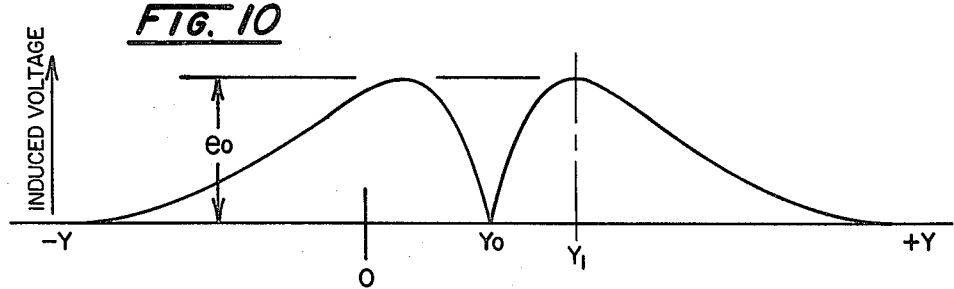
FIG. 10 is another idealized output characteristic curve for the sensor of FIG. 8 (motion along the y axis)

At this juncture, the solenoid is rotated, as discussed above, through 90° to, in turn, displace the field by 90°. The magnetic source coil then is moved from the position $x_0$ along the reference plane and parallel with the y axis and the induced voltage at sensor 14 evolves an output characteristic represented at FIG. 10. Note again, that the maxima of induced voltage, $e_0$, are of equal height confirming the perpendicular orientation of the orientation axis of sensor 14. However, a null point is achieved as the solenoid is effectively moved to position, $y_0$, to locate the y axis coordinate of sensor 14. It should be understood, of course, that value $y_0$ as well as $x_0$ will be located by movement designated along a direction parallel or in some predictable relationship respectively to the x and y axes. Knowing the alignment of the orientation axis of sensor 14, it then becomes necessary to determine the depth thereof from the x-y plane which is labeled, d. As demonstrated earlier, the value, d, is directly related to the distance from null point to peak or maximum value, $e_0$. This is shown in FIG. 10 as the distance between null point, $y_0$ and $y_1$. Of course, for the exemplary arrangement shown, the distance, d, also can be developed in the same manner in conjunction with x axis coordinate location data as represented at FIG. 9.

Figure 11:
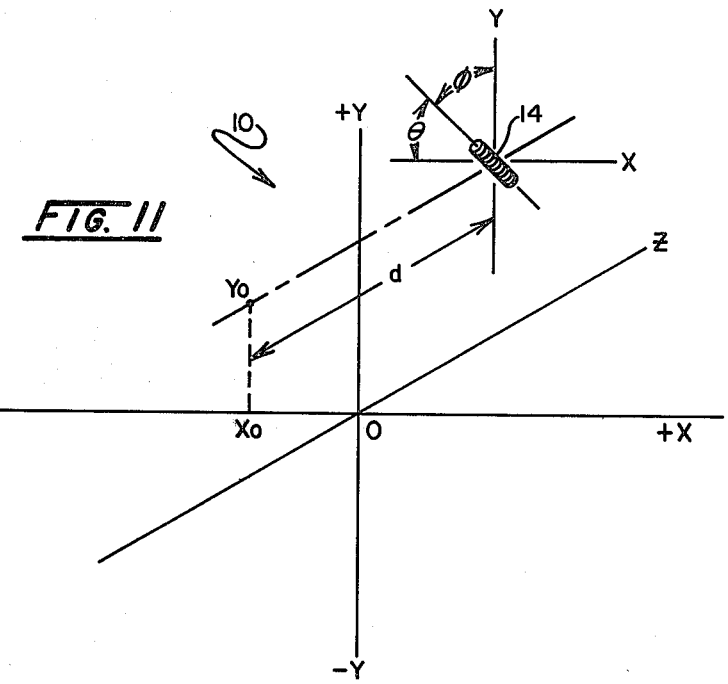
FIG. 11 is an idealized representation of the coordinatized location of a sensor according to the invention in three-dimensional space, the sensor having an angular orientation with respect to a given reference plane.

Looking now to FIG. 11, a next and more typical condition is represented wherein sensor 14 is oriented such that its orientation axis is at an angle, $\phi$, with respect to the y axis and at an angle, $\theta$, with respect to the x axis. As before, a reference plane is developed within which the x and y axes are situate and the sensor 14 is positioned with respect to the latter axes at coordinate location $x_0$, $y_0$. Additionally, the sensor is located at a depth, d, from the x-y plane.

Figure 12:
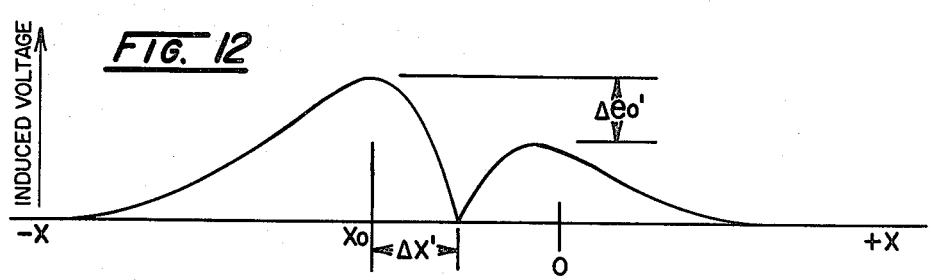
FIG. 12 is an idealized output characteristic curve of the sensor represented in FIG. 11.

Following the technique described above, the solenoid coil either physically or electrically, i.e. "effectively" is moved along (or predictably with respect to) the x axis from the 0,0 origin to evolve an induced voltage output characteristic as represented at FIG. 12. As the characteristic curve reveals, a null point is achieved but, inasmuch as sensor 14 is oriented at an angle, $\phi$, with respect to the x axis, the null point is not representative of the position, $x_0$ of sensor 14. The null point, as shown, is actually positioned a distance $\Delta x'$ from the actual coordinate position, $x_0$ of sensor 14. However, the angle of pitch, $\theta$ is related to the value $\Delta x'$ as well as to the difference in maxima or peaks as shown in FIG. 12 at $\Delta e_0'$ and considered in detail at FIGS. 20 and 22. Thus, knowing the value $\Delta e_0'$, the angle $\theta$ and the value, $\Delta x'$ can be calculated and the true coordinate position, $x_0$ readily determined. [See FIGS. 20 and 22 later herein where $\Delta e$ is plotted with respect to $\theta$ (FIG. 22) and $\Delta e$ is plotted with respect to $\Delta x$ (FIG. 20)].

Figure 13:
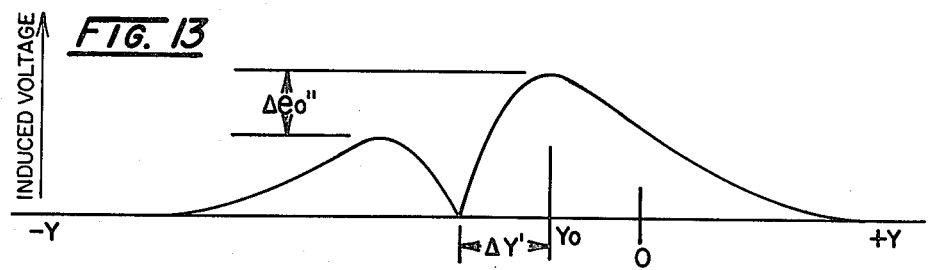
FIG. 13 is another idealized output characteristic curve of the sennsor represented in FIG. 11.

With the value, $x_0$ determined, the solenoid coil is rotated and moved effectively along the y axis or a corresponding predictable route. The result of such movement provides an induced output voltage characteristic of sensor 14 as represented at FIG. 13 wherein a null point is located at a distance $\Delta y'$ displaced from true y axis coordinate, $y_0$. Additionally, and again because of the angular orientation of sensor 14, the maxima or peak values of the characteristic output are of different magnitude to an extent $\Delta e_0'$. As before, this value is directly related to the pitch angle, $\phi$ and can be utilized to determine the value $\Delta_y'$ and thence the coordinate $y_0$. The depth, d, may be determined from the relationship of the distance between the peaks to d for the displacement angle which has been determined. In consequence, as a result of a singular excursion of the solenoid coil along or with respect to the x axis and a singular excursion along or with respect to the y axis, the coordinates $x_0$, $y_0$, depth d, pitch angles $\phi$ and $\theta$ are readily determined.

As indicated earlier herein, the type of sensor coil which is utilized may vary widely in accordance with the desires of the designer. Where incorporated in conjunction with a catheter type device, the winding will be relatively small and positioned near the operating tip of the catheter. Looking to FIG. 14, one such catheter is shown generally at 50 having an outer tip portion 52 about which is provided a coil winding 54, such winding being provided in conventional "woven" fashion to provide improved symmetry about the central axis thereof. Looking additionally to FIG. 15, a catheter 56 is shown wherein the sensor coil thereof, 58, is coupled in articulated fashion through a simple hinge connection 60. With the arrangement, a predetermined amount of cant with respect to the axis of rod portion 56 may be provided or, through manipulation by cables or the like, the winding 58 may be manipulated about coupling 60 while utilized in vivo. For example, sensor portion 58 may be adjusted by the operator such that its axis of orientation is perpendicular to the predetermined reference plane established for the method of the invention. To carry this out, the catheter rod portion 56 may be rotated as represented by the arrow to adjust the pitch angle of the sensor to a position of perpendicularity with respect to one reference plane axis. Following such adjustment, by manipulation through a screw attachment or direct wire attachment to sensor 58 extending through the hollow interior portion of catheter 56, the angle of sensor 58 may be adjusted by pivotal motion thereof in a plane perpendicular to the axis of rotation of the catheter until perpendicularity of its axis of orientation with respect to an opposite axis at the reference plane is achieved.

A variety of implementations of the theory of the invention will occur to those skilled in the art. The most basic approach for the mapping or detection procedure is one wherein the solenoid field source is manually moved along one pre-established reference plane axis and rotated to provide a corresponding field rotation for a second axis. Manual movement of the solenoid then is carried out in a direction parallel to the latter axis. Looking to FIG. 16, a schematic representation of such an approach is revealed. In the figure, a reference plane is established as a hard surface 70 upon which is developed a coordinate grid having x and y axes. The subject 72 within which the sensor 74 is located is positioned below surface 70 and within the influence of a manually manipulated magnetic source 76. This source is excited, for example by an a.c. current from a power source represented at 78. The operator moves magnetic source 76 about surface 70 in correspondence with the predetermined x and y axes to read the corresponding induced output signals of sensor 74 at a visual output device such as a meter or oscilloscope as represented at 80. The output signal developed at sensor 74 generally will be calibrated and amplified by a buffer amplifier stage as represented at 82. The information which the operator requires for this simple procedure is the position corresponding to the null point and the values of the maxima at either side of the null point for manipulation of source 76 along each of the x and y axes. For such data, the operator observes the position of magnetic source 76 and sensor position correlations then can be developed. Various types of meters are available for providing read-out. The oscilloscope may be of a conventional variety or a storage oscilloscope may be utilized to aid the operator.

Referring to FIG. 17, a next approach to the utilization of the theory of the invention is provided. In this schematic representation, the subject 86 is positioned over a planar surface 88 upon which are established position deriving x and y axes. The magnetic source represented at housing 90 is stationary with respect to surface 88 and, in its simplest form, merely may be three windings in delta or star configuration which may be properly excited by an a.c. source to provide a field position and orientation as desired by the operator. Another technique for providing a stationary magnetic source is to utilize a distributed solenoid within housing 90 wherein a series of windings for each axial direction are excited in predetermined sequence to provide, in effect, an electrical movement of the field source. Controlled excitation of the magnetic source within housing 90 is provided from a power source and magnetic controller represented at block 92. As before a sensor as at 94 is provided in combination with some form of probe (not shown) and the induced output signal therefrom is treated by a buffer amplification stage 96 and readout by an appropriate visual read-out device as labeled and represented generally at block 98.

Figure 18:
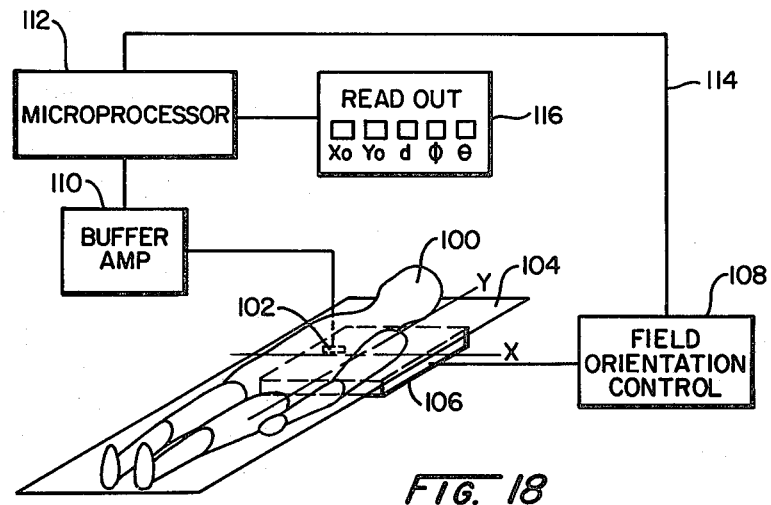
FIG. 18 is a schematic representation of an automated implementation of the method and system of the invention.
Figure 19:
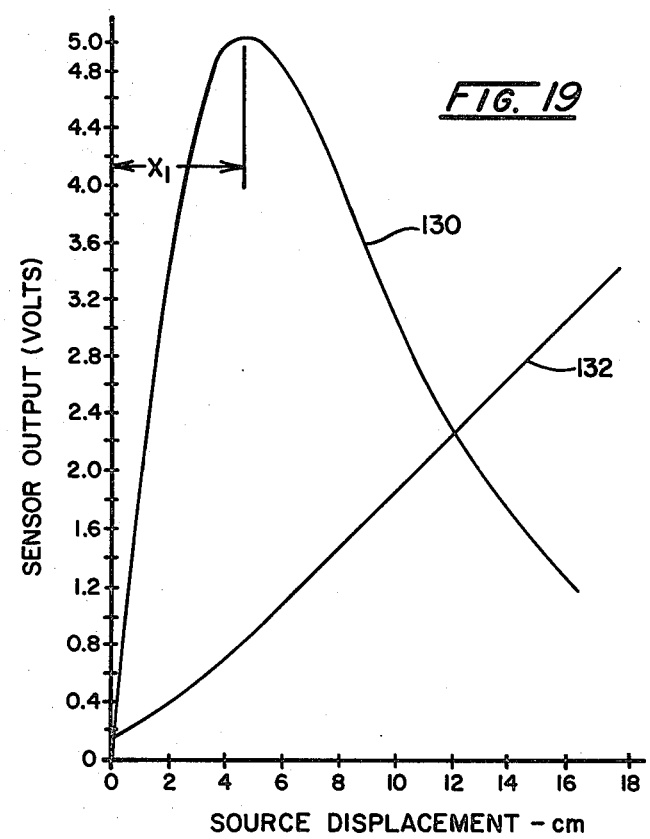
FIG. 19 shows curves plotting data developed in the course of an experiment carried out in verifying the theory of the instant invention.

Another, more sophisticated approach to providing sensor location readout is revealed in connection with FIG. 18. Referring to that figure, the subject 100 within which sensor 102 is located is shown positioned above a reference plane developed by surface 104. Appropriate axes are defined in connection with surface 104 as represented thereupon. The magnetic source provided is a stationary one similar to that described in connection with FIG. 18 and is represented as positioned within box 106. This magnetic source 106 is controlled from a power source and field orientation control function 108 in similar fashion as described in connection with FIG. 17. The induced output of sensor 102 again is treated at a buffer amplification stage 110, the output of which is directed to a microprocessor 112. Microprocessor 112 is coupled by a feedback path represented at line 114 to power source and control function 108. With the arrangement shown, controlling commands are given from microprocessor 112 to control 108 such that the field is caused to move along an x axis, and peak output values as well as null position are recorded. Microprocessor 12 then commands function 108 to move the field to the computed $x_0$ position and hold and, when at position $x_0$ to rotate the magnetic field 90°. Upon completion of such rotation, a command is given to move the field along or parallel to the y axis and provide similar read-outs. Following the appropriate calculation, a readout is provided, as represented at block 116 which appraises the operator of the earlier described $x_0$, $y_0$, d, $\phi$ and $\theta$ values.

Other approaches to implementing the invention will occur to those skilled in the art. For example, the roles of the magnetic source and sensor can be reversed, the sensor being moved to various positions to derive necessary null point and peak value read-outs. However, the availability of smaller size with the sensor coil or the equivalent thereof suggests its more appropriate utilization as located in conjunction with the element being located within the media of investigation. Of considerable advantage, the low level of magnetic field which may be utilized permits wide application in connection with probes contained within living tissue. As indicated above, the strength of the alternating magnetic field which may be employed is generally selected as being lower than that of the earth's magnetic field by several orders of magntiude.

An experimental verification of the invention has been carried out, the results thereof being summarized in connection with the curves represented in FIGS. 19–24. A sensitivity for the system involved of better than 100 $\mu v/\mu m$ and a resolution better than 1 $\mu m$ at a distance of 14 cm from the source were determined. The source coil employed was a solenoid of 400 turns of 23 SWG copper wire on a $\frac{5}{8}$ inch diameter by $\frac{1}{2}$ inch thick former, while the source utilized was a 10 kHz sine wave oscillator. The sensor coil used was a 1 mm diameter $\times$2 mm long, 48 gauge solenoid of 3,000 turns coupled with a TEK 502 oscilloscope. Amplitude output was measured by a digital voltmeter. The source coil was mounted on a gimbal fixed to the cross slide of a traveling microscope. This arrangement premitted angular adjustment of the source coil about a vertical axis, the cylindrical axis of the coil always being in a horizontal plane. The microscope slide allowed an adjustment of $\pm 20$ centimeters along a designated x-axis with an accuracy of better than 1 $\mu m$. The sensor coil was fixed to a glass rod held vertically to a Unimat-SL Lathe which, in turn, was mounted upon a 50 cm compound slide arranged along the predesignated y-axis. Thus, the sensor coil could be adjusted around a vertical axis with the cylindrical axis of the coil in a horizontal plane. The coil also could be adjusted along the predesignated x, y and z axes. With the arrangement, both coils could be adjusted in angular and three-dimensional position to investigate various parameters.

A determination of the linear sensitivity of the system utilizing the geometry represented in FIG. 18 was carried out. The source coil was moved to the origin of the predesignated x-y Cartesian coordinate axes, the axis of symmetry of the source coil being located perpendicular to the x-y plane. The sensor coil was located 9 centimeters from the reference plane along the y axis, its axis of symmetry being in parallel therewith and was moved in steps along the x axis from x=1 to x=16 cm and the sensor output at each step was recorded. Results of this procedure are recorded in FIG. 19 as a curve 130. The distance between the null point, occurring at the origin of the x-y axes, and the peak of the curve ($x_1$) was determined and correlated with depth, the two values being found to have a function, for this particular arrangement, related by a constant of approximately 0.5. The initial positions of response curve 130 were plotted so as to exhibit horizontal data expanded by a factor 10 and vertical data expanded by a factor of 100 and the resultant curve is shown at 132. This reveals an initial slope of 1.9 v/cm to evolve the noted resolution of better than 1 $\mu m$ and a sensitivity of better than 100 $\mu v$/cm.

Figure 20:
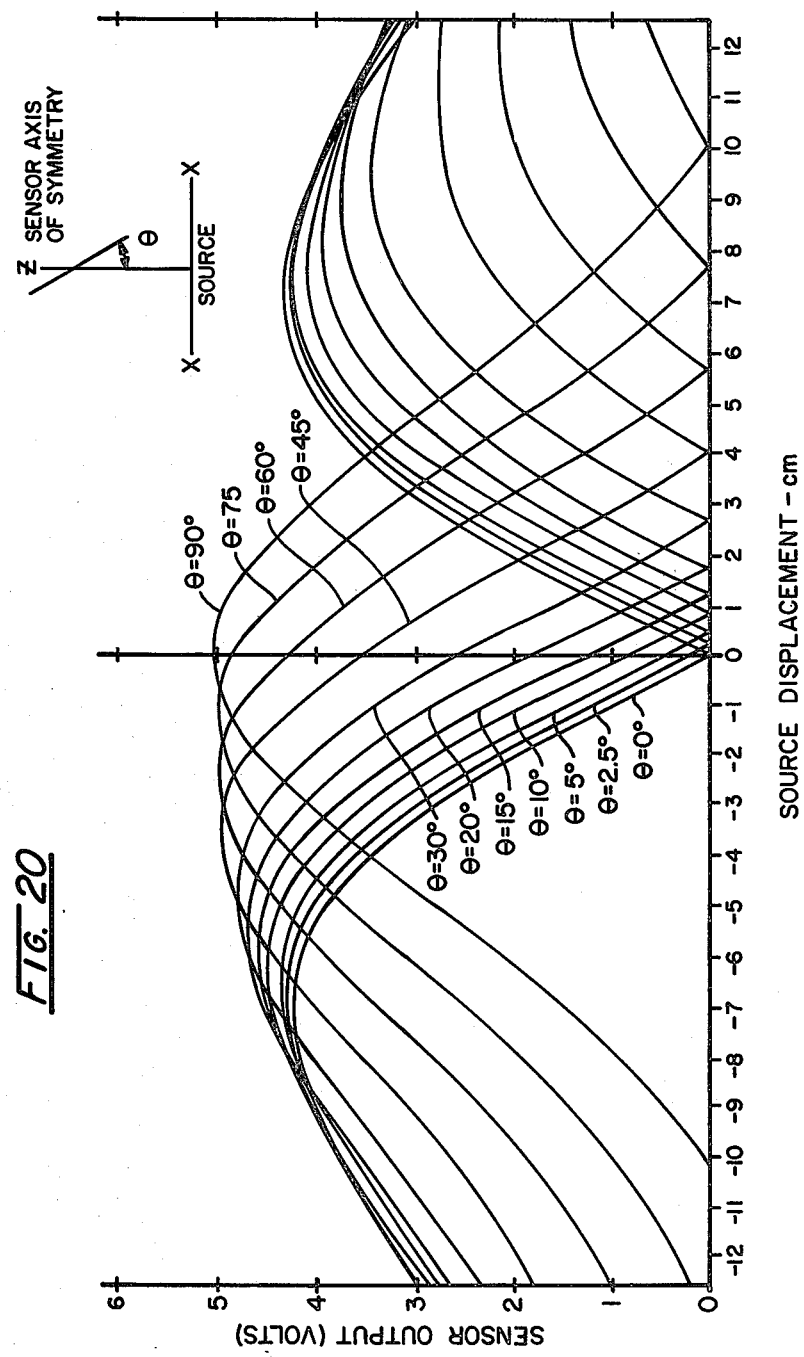
FIG. 20 shows a family of curves correlating source displacement with sensor output for a variation of orientations of the axis of symmetry of such sensor.

Looking to FIG. 20, the plotted results of an investigation wherein the axis of symmetry of the sensor as aligned with the y and z axes but having an angle, $\theta$, varying with respect to the z axis are provided. To generate each curve, the source or coil was moved in 1 centimeter increments from a $-x$ to $+x$ direction along the x axis. The curves at FIG. 20 show that where the angle $\theta$ is 0°, the null point falls at the origin and the maxima are of equal magnitude. However, as the angle $\theta$ is varied by 2.5°, 5° and 15° increments, the maxima at either side of a correspondingly varying null point position alter in magnitude. Thus, a correspondence between the position of null point as well as the difference in magnitude between the peaks is witnessed with a varying pitch of the axis of symmetry of the sensor.

Figure 21:
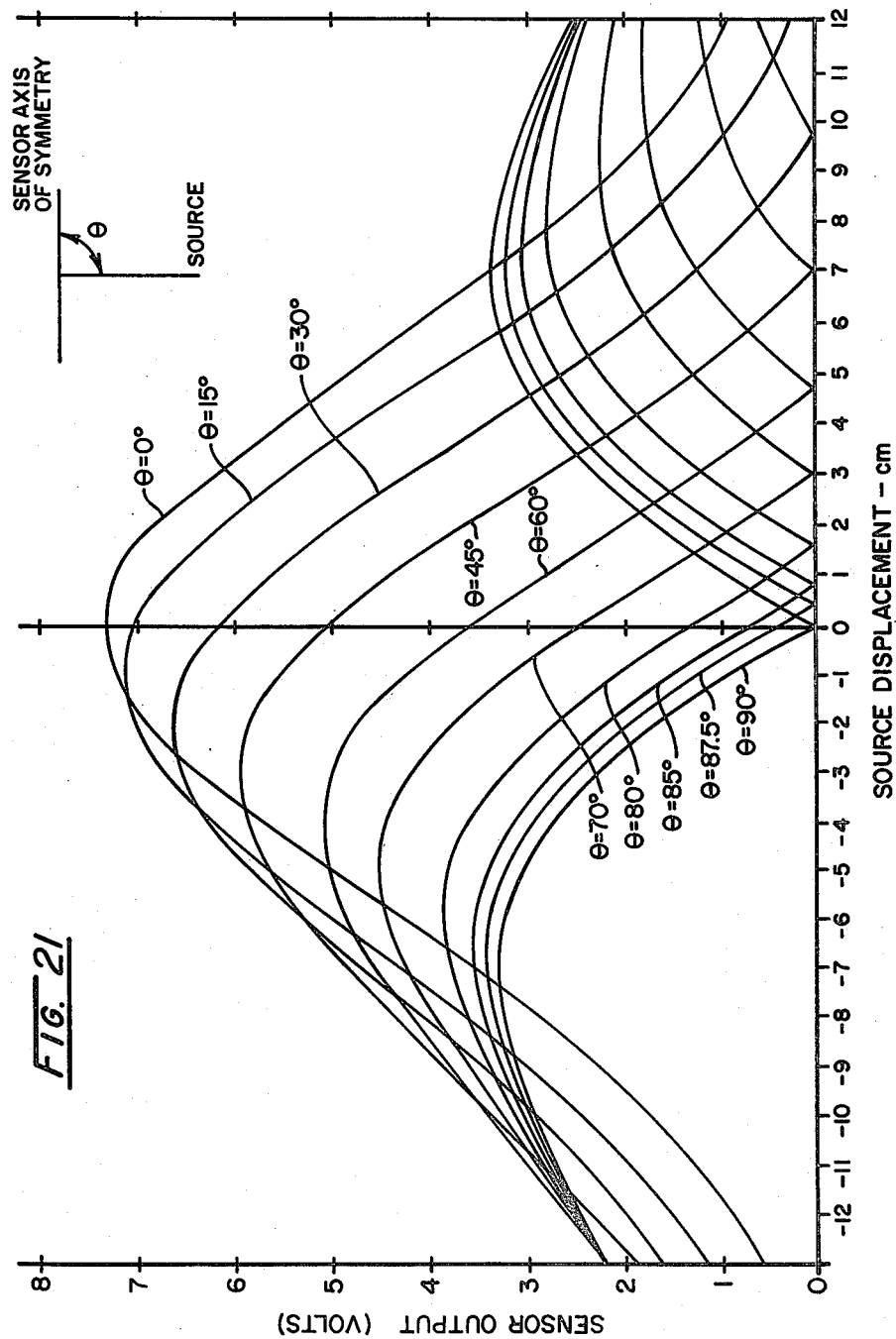
FIG. 21 shows a family of curves developed correlating source displacement with sensor output variation in pitch for the implementation of the invention shown in connection with FIG. 7.

FIG. 21 reveals data corresponding to that developed for FIG. 20 but utilizing the source-sensor geometry as described in connection with FIG. 7. The sensor axis of alignment for this arrangement, as indicated in connection with FIG. 7, was initially aligned with the y axis; the corresponding sensor angle, $\theta$, for that orientation being 90°. The sensor coil was then turned counterclockwise in steps from $\theta = 90°$ to $\theta = 0°$ and, for each of these incremental steps, the source coil position was moved along the x axis from negative toward positive positions and the sensor output at each such position was recorded. The response curves shown in FIG. 21 are characterized by sharp minima or null points and two peaks, one on either side thereof. As in the data derived in connection with FIG. 20, the null point incrementally moves as the difference in maxima between oppositely disposed sides of the curve increases. The data shown in FIG. 21 reveals the higher sensitivity characteristic for the embodiment described in connection with FIG. 7. As indicated earlier herein, data generated in connection with FIGS. 20 and 21 show the difference in maxima heights from which any angle as at $\theta$ readily may be derived. Further, from this data, the earlier-described $\Delta x'$ or $\Delta y'$ components can be established to, in turn, find the corresponding positions $x_0$ and $y_0$. It may be recalled from the discussion in connection with FIG. 15, that catheter 56 sensor coil 58 may be manipulated by rotation and through internal connection of cables to articulated joint 60. The sensor thus may be manipulated, in vivo, until such time as the two maxima peaks are of equal intensity. When this occurs, notwithstanding an arbitrary orientation of catheter 56, the sensor will be aligned for the particular FIG. 1 or FIG. 7 detection mode desired with respect to the pre-established reference plane.

Looking to FIG. 22, the differences between the right and left peak values as set forth in FIG. 20 are plotted with respect to the angle $\theta$ between the sensor axis of symmetry and the z axis. Note the near linearity involved in this relationship.

As indicated earlier herein, rather than carrying out a physical movement and rotation of the source coil, various electrical switching techniques and the like utilizing stationary coils may be found preferable. For example, through the utilization of three 120° spaced coils, the net field may be rotated essentially in any desired direction. Curves 134 and 136 in FIG. 23 relate the difference in output magnitude of right and left peaks with respect to variations in sensor coil angle, $\theta$ as described immediately above. Where the degree of rotation of the source varies to values other than the 90° rotation described above, the question arises as to whether the linear relationship was established, for example, in connection with the data deriving the curve of FIG. 22, still obtains. Curve 134 plots corresponding voltage amplitude difference values for a 45° rotation of the source coil, while curve 136 carries out derivation of the same data for a 60° rotation of the source coil. Data deriving the above curves is plotted with respect to variations in the angle, $\theta$ of the sensor coil in similar fashion as described in connection with FIG. 22. Note, that the linear relationship remains to assure the validity of the inventive technique for variations in source inclination.

Finally, referring to FIG. 24, the results of an investigation for the condition wherein the axis of symmetry of the source coil is canted with respect to the reference or x-y plane are revealed. In this experiment, the source coil was canted as labeled, by values of 10, 20 and 40 degrees with respect to the source plane and moved incrementally along the x axis under an experimental arrangement corresponding with the geometry of FIG. 1. The results shown reveal that the variation of source angle with respect to the reference plane merely occasions an alteration in sensitivity and resultant peak values. As a consequence, where peak values are utilized, then such data as is represented in FIG. 22 is necessary for evolving proper sensor location derivations.

Since certain changes may be made in the above method and system without departing from the scope of the invention herein involved, it is intended that all matter contained in the above description or shown in the accompanying drawings shall be interpreted as illustrative and not in a limiting sense.

We claim:

1. The process for determining the location and orientation in space of a magnetic field responsive sensor having an output signal in the presence of a magnetic flux linkage comprising the steps of:

defining a plane within which are established first and second intersecting reference axes for deriving the position of said sensor with respect to said axes;

providing a magnetic field source movable with respect to said plane to derive alternating magnetic flux fields;

effectively moving said magnetic field source parallel to said first reference axis and determining, from said sensor output signal, locations representing a first null point of substantially no said flux linkage, those first and second locations on each side of said first null point representing maximum said flux linkage and the magnitudes of said sensor output signal values at said first and second locations;

effectively moving said magnetic field source parallel to said second reference axis and determining, from said sensor output signal, locations representing a second null point of substantially no said flux linkage, those third and fourth locations on each side of said second null point representing maximum said flux linkage and the magnitudes of said sensor output signal values at said third and fourth locations;

determining said sensor position geometrically most proximate said first axis as a function of said first null point location and the magnitude of the output difference between said sensor output signal values at said first and second locations;

determining said sensor position geometrically most proximate said second axis as a function of said second null point location and the magnitude of the output difference between said sensor output signal values at said third and fourth locations; and determining the geometrically most proximate distance of said sensor from said plane as a function of the location of one of said null points, an adjacent location of maximum said flux linkage and a corresponding said difference between said magnitudes of said sensor output values associated with a given one of said first or second axes.

2. The process of claim 1 wherein said sensor component is provided as a winding configured or substantially symmetrically disposed about an orientation axis.

3. The process of claim 1 wherein said first and second axes are mutually orthogonally disposed in said plane.

4. The process of claim 1 wherein said magnetic field source is provided at said defined plane.

5. The process of claim 1 wherein said magnetic field source is effectively moved along said first axis in a manner wherein said field is substantially symmetrically disposed thereabout.

6. The process of claim 1 wherein said magnetic field source is effectively moved along a locus of travel in parallel with said second axis in a manner wherein said field is substantially symmetrically disposed thereabout.

7. The process of claim 1 wherein said magnetic field source is excitable from an alternating current source.

8. The process of claim 1 wherein said magnetic field source is provided having an axis of field orientation about which said alternating magnetic flux fields are symmetrically disposed, said field orientation axis being substantially perpendicular to said defined plane.

9. The process of claim 8 in which said sensor component is configured as a winding substantially symmetrically disposed about an orientation defining axis, said orientation defining axis being generally disposed in parallel relationship with said defined plane.

10. The process of claim 8 in which said sensor component axis of orientation is effectively oriented in generally parallel relationship with said first axis when said magnetic field source is moved therealong.

11. The process of claim 8 in which said sensor component axis of orientation is effectively oriented in generally parallel relationship with said second axis when said magnetic field source is effectively moved in parallel therewith.

12. The process of claim 8 in which said sensor component comprises:
a first magnetic field responsive winding symmetrically disposed about a first said axis of orientation; and
a second magnetic field responsive winding symmetrically disposed about a second said axis of orientation transversely disposed with respect to said first axis of orientation.

13. The process of claim 8 in which:
said sensor component is configured as a winding substantially symmetrically disposed about an orientation defining axis, said orientation defining axis being generally disposed in parallel relationship with said defined plane; and
said sensor component axis of orientation is effectively oriented in generally parallel relationship with said first axis when said magnetic field source is moved therealong.

14. The process of claim 1 in which:
said sensor component is provided as a winding configured as substantially symmetrically disposed about an orientation axis; and
wherein said first and second axes are mutually orthogonally disposed in said plane.

15. The process of claim 1 in which:
said first and second axes are mutually orthogonally disposed in said plane; and
said magnetic field source is provided at said defined plane.

16. The process of claim 1 in which:
said sensor component is provided as a winding configured as substantially symmetrically disposed about an orientation axis; and
said magnetic field source is effectively moved along said first axis in a manner wherein said field is substantially symmetrically disposed thereabout.

17. The process of claim 16 in which:
said magnetic field source is effectively moved along said first axis in a manner wherein said field is substantially symmetrically disposed thereabout; and
said magnetic field source is effectively moved along a locus of travel in parallel with said second axis in a manner wherein said field is substantially symmetrically disposed thereabout.

18. The process of claims 15, 16 or 17 in which said magnetic field source is excitable from an alternating current source.

19. The process of claim 2 wherein said step determining said sensor position geometrically most proximate said first axis is carried out by initially determining the magnitude of the difference between said sensor output values for said first and second locations representing maximum said flux linkage;
correlating said magnitude with the extent of angular deviation of said orientation axis from said first axis to derive a first error value; and
combining said first error value with said first null point location to establish said sensor position.

20. The process of claim 5 in which:
said sensor component is present as a winding substantially symmetrically disposed about an orientation axis; and said orientation axis is disposed substantially perpendicular to said plane.

21. The process of claim 20 in which said magnetic field source is effectively moved along a locus of travel in parallel with said second axis in a manner wherein said field is substantially symmetrically disposed thereabout.

22. The process of claim 21 wherein said magnetic field source is excitable from an alternating current source.

23. The process for determining the location in space of a predetermined portion of an elongate probe comprising the steps of:
providing a sensor connected with said probe predetermined portion and effectively pivotally movable thereupon, said sensor being present as a varying magnetic field responsive winding disposed about an orientation axis and having output signals in the presence of magnetic flux linkage;
defining a reference plane within which are established first and second intersecting reference axes for deriving the position of said sensor with respect to said reference axes;
providing a magnetic field source effectively movable with respect to said reference plane, excitable from an alternating current source to derive alternating magnetic flux fields;
effectively moving said magnetic field source along a first locus in parallel with said first axis and determining, from said output signals, locations along said locus representing a first null point of substantially no said flux linkage, those first and second locations on each side of said null point representing maximum said flux linkage and the magnitudes of said sensor output signal values at said first and second locations;
effectively moving said magnetic field source along a second locus in parallel with said second axis and determining, from said sensor output signals, locations along said second axis representing a second null point of substantially no said flux linkage, those third and fourth locations on each side of said second null point representing maximum said flux linkage and the magnitudes of said sensor output signal values at said third and fourth locations;

determining said sensor position with respect to said first reference axis as a function of said first null point location and the magnitude of the output difference between said sensor output signals for said first and second locations and said sensor position with respect to said second axis as a function of said second null point location and the magnitude of the output difference between said sensor output signals for said third and fourth locations; and determining the geometrically most proximate distance of said sensor from said reference plane as a function of the location of one of said null points and an adjacent location of maximum said flux linkage.

24. The process of claim 23 including the steps of:

moving said sensor in a first sense and repeating said effective movement of said magnetic field source along said first locus until the magnitude of said signals representing maximum said flux linkage are substantially equal to derive corrected said first null point and first and second maximum flux linkage locations following said effective movement of said source along said first locus;

moving said sensor in a second sense and repeating said effective movement of said magnetic field source along said second locus until the magnitude of said signals representing maximum said flux linkage are substantially equal to derive corrected said second null point and third and fourth maximum flux linkage locations following said effective movement along said second locus;

said determination of said sensor position with respect to said first reference axis is in correspondence with said corrected first null point location and said sensor position with respect to said second axis is in correspondence with a said corrected second null point location; and said determination of the geometrically most proximate distance of said sensor from said reference plane is correspondence with the location of a said corrected null point and an adjacent corrected maximum flux linkage location.

25. The process of claim 24 in which said sensor movement in said first sense is carried out by the rotation thereof.

26. The process of claim 25 in which said sensor movement in said second sense is carried out by the pivotal movement thereof upon said probe within a plane perpendicular to the axis of said rotation of said sensor.

27. The process of claim 26 wherein said magnetic field source is effectively moved along said first and second loci in a manner wherein said field is substantially symmetrically disposed thereabout.

28. The process of claim 23 wherein:

said magnetic field source is provided having an axis of field orientation about which said alternating magnetic flux fields are symmetrically disposed, said field orientation axis being substantially perpendicular to said reference plane.

29. The process for determining the location in space of an implement comprising the steps of:

providing a magnetic field source attached to said implement and excitable from an alternating current source to derive alternating magnetic flux fields;

defining a reference plane within which are established first and second intersecting axes for deriving the position of said field source with respect to said axes;

providing a sensor as a varying magnetic field responsive component having an orientation defining axis and having output signals in the presence of magnetic flux linkage therewith;

effectively moving said sensor with respect to said reference plane along a first locus parallel to said first axis and determining from said output signals, locations along said first locus representing a first null point of substantially no said flux linkage, those first and second locations on each side of said first null point representing maximum said flux linkage and the magnitudes of said sensor output signal values at said first and second locations;

effectively moving said sensor along a second locus parallel to said second axis and determining from said output signals locations along said second axis representing a second null point of substantially no said flux linkage, those third and fourth locations on each side of said second null point representing maximum said flux linkage and the magnitudes of said sensor output signal values at said third and fourth locations;

determining said magnetic field source position geometrically most proximate to said first axis as a function of said first null point location and the magnitude of the difference between said sensor output values for said first and second locations;

determining said sensor position geometrically most proximate to said second axis as a function of said second null point location and the magnitude of the difference between said sensor output signal values for said third and fourth locations; and determining the geometrically most proximate distance of said magnetic field source from said reference plane as a function of the location of a said null point, an adjacent location of maximum said flux linkage and a corresponding said difference between said magnitudes of said sensor output signal values associated with a given one of said first or second axes.

30. A system for determining the location in space of an implement comprising:

a sensor connectable with said implement and present as a varying magnetic field responsive component substantially symmetrically disposed about an orientation axis and having output signals in the presence of magnetic flux linkage therewith;

means defining a reference plane at which are established first and second intersecting axes for deriving coordinate data representing the position of said sensor with respect to said axes;

a magnetic field source positioned at said plane and excitable from an alternating current source to derive alternating magnetic flux fields;

means for effectively moving said magnetic field source along a first locus parallel with said first axis and thence along a second locus parallel with said second axis;

output means responsive to said sensor output signals for deriving outputs dependent upon the locations of said magnetic field source at said plane, corresponding with null points of substantially no said flux linkage, and corresponding with those two locations on each side of a given said null point representing maximum said flux linkage, said outputs further being dependent on the magnitudes of said signals; and means for determining the difference between the magnitudes of said sensor output signals at said two locations.

31. The system of claim 30 in which said sensor component is a coil, the windings of which are substantially symmetrically disposed about said orientation axis.

32. The system of claim 31 in which said sensor coil is pivotally mounted upon said implement.

* * * * *